United States Patent [19]
Marshall et al.

[11] Patent Number: 6,045,561
[45] Date of Patent: Apr. 4, 2000

[54] SURGICAL KNOT MANIPULATOR

[75] Inventors: Stuart C. Marshall, La Jolla, Calif.; Jeffry B. Skiba, Phoenix, Ariz.

[73] Assignee: Orthopaedic Biosystems Ltd., Inc., Scottsdale, Ariz.

[21] Appl. No.: 09/103,517

[22] Filed: Jun. 23, 1998

[51] Int. Cl.⁷ .................................................. A61B 17/64
[52] U.S. Cl. ........................................ 606/148; 606/139
[58] Field of Search ................................ 606/148, 139, 606/144

[56] References Cited

U.S. PATENT DOCUMENTS

| | | | |
|---|---|---|---|
| 4,935,027 | 6/1990 | Yoon | 606/146 |
| 5,334,200 | 8/1994 | Johnson | 606/148 |
| 5,364,408 | 11/1994 | Gordon | 606/144 |
| 5,403,330 | 4/1995 | Tuason | 606/148 |
| 5,405,352 | 4/1995 | Weston | 606/148 |
| 5,447,512 | 9/1995 | Wilson et al. | 606/139 |
| 5,496,331 | 3/1996 | Xu et al. | 606/139 |
| 5,501,688 | 3/1996 | Whiteside et al. | 606/103 |
| 5,549,618 | 8/1996 | Fleenor et al. | 606/148 |
| 5,693,061 | 12/1997 | Pierce et al. | 606/148 |
| 5,752,964 | 5/1998 | Mericle | 606/148 |

Primary Examiner—Michael Buiz
Assistant Examiner—Anthony King
Attorney, Agent, or Firm—Laura J. Zeman; Snell & Wilmer, L.L.P.

[57] ABSTRACT

A surgical knot manipulator device is presented for facilitating the tying and untying of surgical knots through an access portal such as an arthroscopic cannula or an endoscopic trocar. The surgical knot manipulator device includes an elongated, cylindrical body member having a handle at its proximal end and a circular loop located at its distal end where the circular loop may contain a slot to facilitate the engagement of a suture.

5 Claims, 2 Drawing Sheets

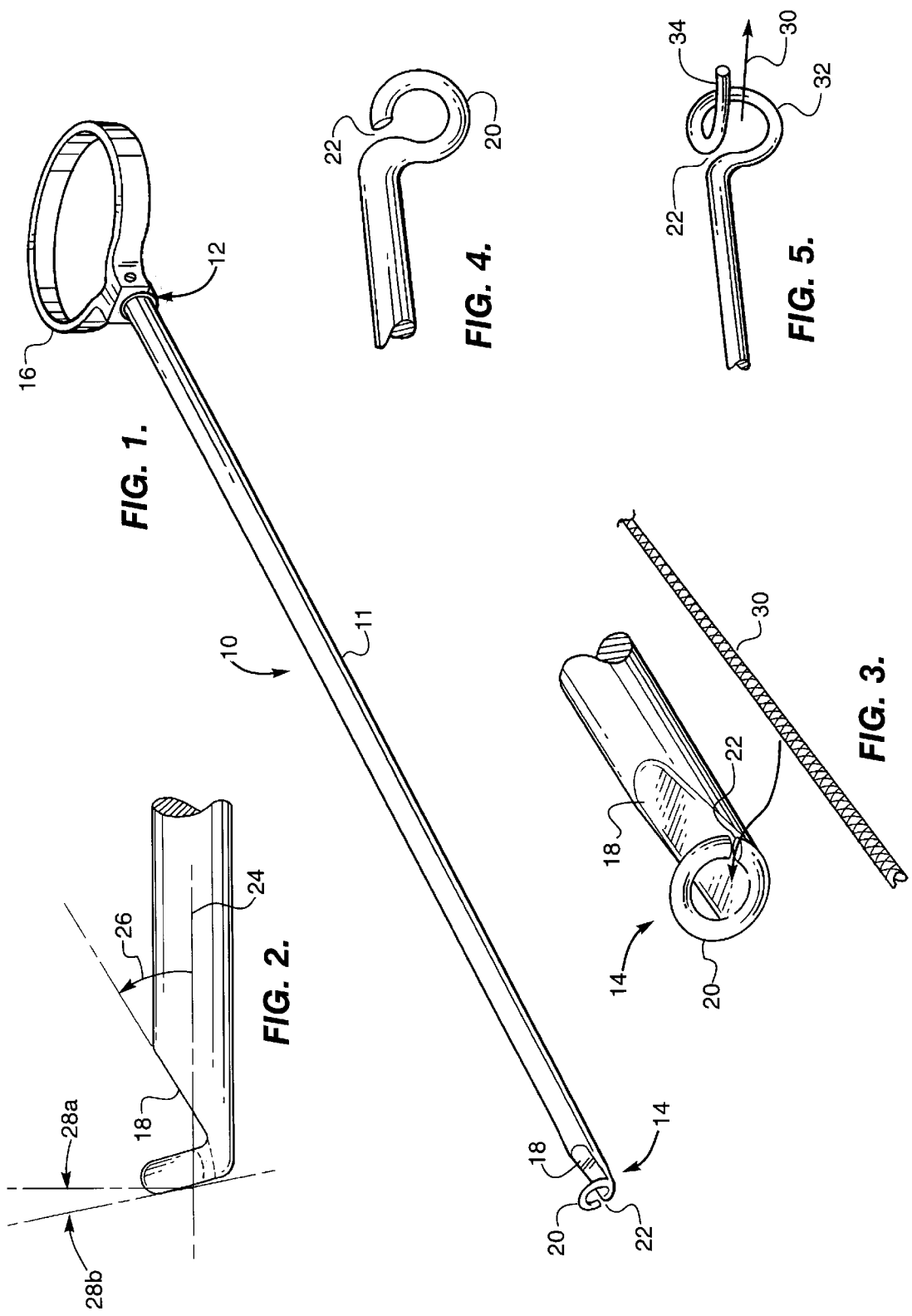

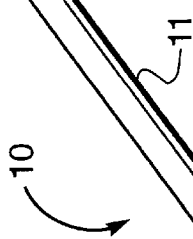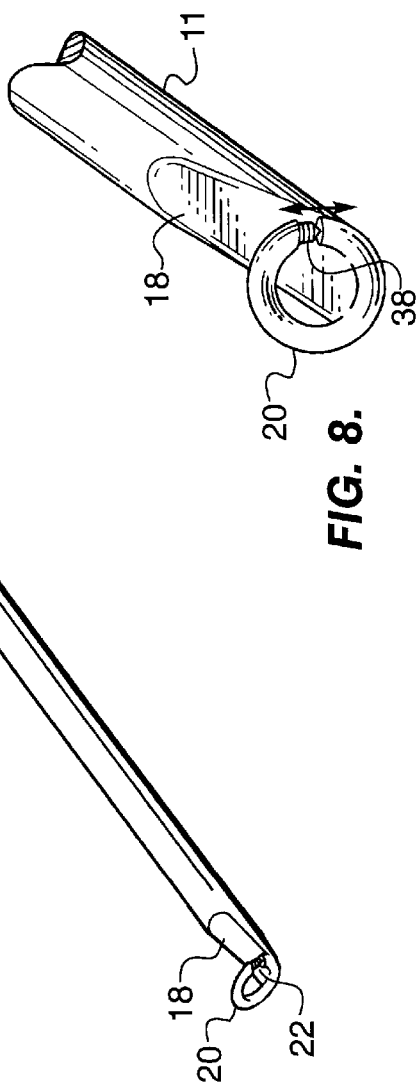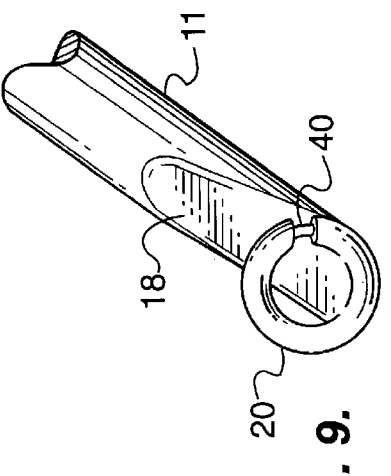

SURGICAL KNOT MANIPULATOR

FIELD OF THE INVENTION

The present invention relates generally to medical instruments. More particularly, the present invention relates to a device for manipulating surgical knots that are tied either openly or through an access portal such as an arthroscopic cannula or an endoscopic trocar. The surgical knot manipulator device removes the need for threading the eyelet found on conventional knotting devices and has a slot cut into a portion of the device that manipulates the suture thereby allowing the suture to slip onto the device at any point in the sliding of the throw of the knot. The surgical knot manipulator device is configured with a smooth, cylindrical tip, thereby minimizing suture damage and decreasing any resistance to sliding against the suture when the cylindrical tip contacts the suture.

BACKGROUND OF THE INVENTION

In arthroscopic and endoscopic surgery, surgical knots are tied and passed through a cannula. This procedure presents the surgeon with the task of loading the suture into, or through, a knot manipulator and "pushing" or "pulling" the knot through the cannula. This loading process can be likened to the threading of a needle and can be difficult for the surgeon when the suture is braided or when he is working with gloved hands.

Several knot pusher type devices are known. These knot pusher devices are designed to push suture knots which have been tied extracorporeally or outside of the body during a surgical procedure toward the tissue to be sutured. Many of these devices then function to cut the suture strands once the suture knot has been tied in its proper position. For example, U.S. Pat. No. 5,403,330 issued to Tuason discloses an improved laparoscopic suture knot pusher having an elongated, slender shaft having one end which serves as a handle and another end which serves as a guide for pushing surgical knots forward toward their intended site. The knot pusher guide end is slightly convexed and includes three hollowed-out spaces for receiving and engaging the throws and strands from throw knots that are delivered through a trocar. One of the hollowed-out spaces is a slot that runs across a midsection of a slightly convexed surface that has a spheroidal shaped configuration at the distal end of the shaft.

Another example of a surgical knot pusher is described in U.S. Pat. No. 5,752,964 issued to Mericle. The Mericle patent discloses a surgical knot pusher for pushing a suture knot along a suture strand. The Mericle surgical knot pusher includes an elongated tube with a flattened tip formed on the distal end of the tube. The flattened tip is slotted and provided with an eyelet which restricts the suture and prevents it from falling out of the flattened tip. The suture is easily positioned without threading by pushing the slot on the tip against the suture, thereby forcing the suture through the slot and into the eyelet. A movable rod member having a cutting blade is also affixed to the inside of the distal end of the elongated shaft to provide a cutting device for the suture.

A method and apparatus for placing and tying a knot is also disclosed as a knot pusher assembly in U.S. Pat. No. 5,549,618 issued to Fleenor et al. This apparatus includes a suture knot pusher tube having a distal end slot and an inner concentric tube positioned within the pusher tube where the inner concentric tube also has a distal end slot. The pusher tube and inner concentric tube are movable with respect to one another such that their distal end slots may be aligned or unaligned. The suture can be cut by placing it into the aligned distal slots and then misaligning those slots by moving the pusher tube and inner concentric tube with respect to one another. Further, a knot puller instrument for aiding a surgeon in tying surgical knots is disclosed in U.S. Pat. No. 5,693,061 issued to Pierce et al. The apparatus includes an elongated main body having a linear central longitudinal axis and proximal and distal end portions. The proximal end provides a handle for gripping and the distal end includes a pair of spaced-apart appendages that are positioned to hold a length of suture between them at a transverse, concavely shaped bridge portion. A space between the appendages is formed by suspending one appendage free from the instrument body and connecting the appendage only to the bridge member. During use, the surgeon engages a length of suture with the transverse curved bridge connector by placing it between the two appendages. The surgeon then forces the main body in a desired direction to pull one of the suture-free ends away from the knot being formed, thereby applying tension that helps to tie a knot.

Although several of the previously described devices eliminate the need for threading an eyelet when forming and tying surgical knots during endoscopic and laparoscopic surgery, there is a need for a surgical knot manipulator which allows the suture to be slipped onto the device at any point in the sliding of the throw of a knot.

SUMMARY OF THE INVENTION

It is a principal object of the present invention to provide a surgical knot manipulator to facilitate the tying and untying of surgical knots in arthroscopic and endoscopic surgery.

It is a further object of the present invention to provide a surgical knot manipulator for facilitating the tying and untying of surgical knots which eliminates the need for threading suture through an eyelet.

It is still a further object of the present invention to provide a surgical knot manipulator for facilitating the tying and untying of surgical knots which allows the suture to slip onto the device at any point in the sliding of the throw of the knot.

It is yet a further object of the present invention to provide a surgical knot manipulator for facilitating the tying and untying of surgical knots which minimizes suture damage and decreases resistance between the suture and the suture knot manipulator when sliding suture against the suture knot manipulator device.

In brief, there is provided a suture knot manipulator device which includes an elongated, cylindrical body member having a proximal end and a distal end, a handle located at the proximal end, and a circular ring member located at the distal end.

These and other objects, features and advantages of the present invention will become more apparent to those skilled in the art from the following more detailed description of the non-limiting preferred embodiments of the invention taken with reference to the accompanying figures.

BRIEF DESCRIPTION OF THE DRAWINGS

FIG. 1 is a perspective view of a first embodiment of the surgical knot manipulator device of the present invention.

FIG. 2 is an enlarged side elevational view of the distal end of the surgical knot manipulator device shown in FIG. 1.

FIG. 3 is a partial perspective view of the distal end of the surgical knot manipulator device shown in FIG. 1 having a slot on the opposite side of the continuous ring member.

FIG. 4 is an enlarged perspective view of the distal end of a second embodiment of the surgical knot manipulator device of the present invention.

FIG. 5 is an enlarged perspective view of the distal end of a third embodiment of the surgical knot manipulator device of the present invention.

FIG. 6 is an enlarged perspective view of the distal end of a fourth embodiment of the surgical knot manipulator device of the present invention.

FIG. 7 is a perspective view of a fifth embodiment of the surgical knot manipulator device of the present invention.

FIG. 8 is an enlarged perspective view of the distal end of the surgical knot manipulator device of the present invention shown in FIG. 7.

FIG. 9 is an enlarged perspective view of the distal end of a sixth embodiment of the surgical knot manipulator device of the present invention.

DETAILED DESCRIPTION OF THE PREFERRED EMBODIMENTS

Referring now to the figures, where like reference numbers refer to similar elements, FIG. 1 illustrates a perspective view of a first embodiment of the surgical knot manipulator device 10 of the present invention. The first embodiment of the surgical knot manipulator device 10 comprises an elongated, cylindrical body member 11 having a proximal end 12 and a distal end 14. A swivel handle 16 is attached to the proximal end 12 of the elongated, cylindrical body member 11 such that the swivel handle member 16 can rotate about the circumference of the proximal end 12 of the elongated, cylindrical body member 11. The distal end 14 of the elongated, cylindrical body member 11 comprises an electropolished tip which includes a smooth surface incline 18 which is formed from a cut angle at the distal end 14 and a circular loop 20 which extends contiguously from the smooth surface incline 18. The circular loop 20 includes a slot 22 which allows a suture to pass into the circular loop 20 without threading the suture through the circular loop 20. The slot 22 may be present on any side of the circular loop 20. Further, the circular loop 20 may form a continuous closed circle without a slot as shown in FIG. 6. However, with the embodiment shown in FIG. 6, it is necessary to thread the suture through the circular loop 20 at the distal end 14 of the surgical knot manipulator device 10. It should be noted that the swivel handle 16 may also be configured to form a stationary handle.

Turning now to FIG. 2, there is shown an enlarged side elevational view of the distal end 14 of the surgical knot manipulator device 10 shown in FIG. 1. The smooth surface incline 18 is formed by cutting an angle at approximately 15 to 30 degrees at the distal end 14 of the elongated, cylindrical body member 11 relative to the longitudinal axis of the elongated, cylindrical body member 11 which is depicted by line 24. Arc 26 represents the 15 to 30 degree cut angle. In addition, the circular loop 20 is offset by about 15 to 20 degrees from a right angle (or a 90 degree angle) formed with the longitudinal axis 24 of the elongated, cylindrical body member 11. This 15 to 20 degree offset angle is shown by arrows 28A and 28B. Preferably, the surgical knot manipulator device is formed from an aluminum or metal and is approximately 5 to 10 inches in length for orthopaedic surgery use and approximately 8 to 15 inches in length for laparoscopic surgery use. The circular loop 20 is approximately 0.070 to 0.100 inches in diameter. There is a full radius on all surfaces contacting the suture, and the circular tip configuration comprises an entirely electropolished surface to facilitate the sliding of the suture and the tying and untying of suture knots.

FIG. 3 shows a partial perspective view of the distal end of the surgical knot manipulator device shown in FIG. 1 having a slot 22 located on the opposite side of the continuous ring member or circular loop 20. In utilizing the surgical knot manipulator device 10, the suture 30 may be inserted in the slot 22 at any point along the length of the suture 30, thereby facilitating the tying and untying of suture knots. In tying a suture knot, the ends of a suture which has been sewn through tissue may be crossed over one another and either end of the suture 30 may be inserted in the slot 22 of the surgical knot manipulator device 10. The circular loop 20 is then used to push the suture tie down through an arthroscopic cannula or endoscopic trocar in order to form a knot at the tissue site. The distal end 14 of the elongated, cylindrical body member 11 of the surgical knot manipulator device 10 may be machined and then electropolished to facilitate suture manipulation.

Alternative embodiments of the distal end 14 of the elongated, cylindrical body member 11 of the surgical knot manipulator device 10 are shown in FIGS. 4 and 5. Specifically, FIG. 4 shows an enlarged perspective view of the distal end of the second embodiment of the surgical knot manipulator device 10 of the present invention. The second embodiment of the distal end 14 of the elongated cylindrical body member 11 comprises a circular loop 20 which is formed by bending the distal end of the elongated, cylindrical body member 11. The distal end 14 of the elongated, cylindrical body member 11 is bent in a circular shape such that the very distal end of the elongated, cylindrical body member 11 stops short of meeting or touching an outer surface of the elongated, cylindrical body member 11 thereby forming a slot for accessing the suture. An enlarged perspective view of the distal end of the third embodiment of the surgical knot manipulator device 10 of the present invention is illustrated in FIG. 5 which shows a bent wire which comprises the circular loop 20 of the distal end 14 of the elongated, cylindrical body member 11. More particularly, the distal end 14 of the elongated, cylindrical body member 11 may terminate in a thin wire 32 which may be bent to form a circular loop 20 which culminates in a hook 34.

The closed circle embodiment of the surgical knot manipulator device 10, as previously described, is shown in FIG. 6. Here, the circular loop 20 is completely closed and is contiguous with the smooth surface incline 18 of the elongated, cylindrical body member 11. However, a suture must be threaded through the closed circular loop 20 in order to utilize this embodiment.

Turning now to FIG. 7, there is shown a perspective view of the fifth embodiment of the surgical knot manipulator device 10 of the present invention. The fifth embodiment of the surgical knot manipulator device 10 shown in FIG. 7 is much the same as the first embodiment of the surgical knot manipulator device 10 shown in FIG. 1. However, the embodiment shown in FIG. 7 includes an actuator member 36 which can be used to manipulate the opening and closing of the circular loop 20 of the surgical knot manipulator device 10. The open and close feature of the circular loop 20 is shown more clearly in FIG. 8. FIG. 8 is an enlarged perspective view of the distal end of the surgical knot manipulator device 10 of the present invention shown in FIG. 7. A retracting bar member 38 may be drawn back into a hollowed-out circular loop 20 to allow the entry of a suture by manipulating the actuator member 36. However, unlike the embodiment shown in FIG. 1, the circular loop 20 shown in this embodiment must include a hollowed-out area for the extension and retraction of the retracting bar member 38.

Still another embodiment of the surgical knot manipulator device 10 of the present invention is shown in FIG. 9. FIG. 9 shows an enlarged perspective view of the distal end of the sixth embodiment of the surgical knot manipulator device 10. In this embodiment, a bendable wire 40 extends from the circular loop 20 such that it reaches across the slot 22. In that the wire is bendable, a suture can be easily inserted into the circular loop 20 by applying force to the bendable wire 40. A one-way gate may also be provided to prevent the wire from bending backwards once the suture has been retained within the circular loop 20. Like the previously described embodiments, with the exception of the embodiment shown in FIG. 6, this configuration of the circular loop eliminates the need for threading the suture.

While the preferred forms of the invention have been shown in the drawings and described, since variations in the preferred forms will be apparent to those skilled in the art, the invention should not be construed as limited to the specific forms shown and described, but instead as set forth in the following claims.

We claim:

1. A surgical knot manipulator device comprising:

an elongated, cylindrical body member having a proximal end and a distal end wherein a smooth surface incline is formed with a reduced diameter continuously within a surface of the cylindrical body member near its distal end;

a handle located at the proximal end of the body member; and a circular ring member located at the distal end of the body member.

2. The surgical knot manipulator device of claim 1 wherein the circular ring member is contiguous with the smooth surface incline.

3. The surgical knot manipulator of claim 1 further comprising a slot located within the circular ring member.

4. The surgical knot manipulator of claim 3 further comprising a retracting bar member which extends across the slot and an actuator member for activating the retracting bar member.

5. The surgical knot manipulator of claim 1 wherein said handle is a swivel handle which rotates about the outer circumference of the proximal end of the elongated, cylindrical body member.

* * * * *